United States Patent [19]

Hsu

[11] Patent Number: 6,060,325
[45] Date of Patent: May 9, 2000

[54] DETECTION AND MONITORING OF TOXIC HALOGENATED COMPOUNDS

[75] Inventor: Chang Samuel Hsu, Bridgewater, N.J.

[73] Assignee: Exxon Research and Engineering Company, Florham Park, N.J.

[21] Appl. No.: 08/931,563

[22] Filed: Sep. 16, 1997

[51] Int. Cl.[7] .................................................. G01N 33/00
[52] U.S. Cl. ........................ 436/124; 436/125; 436/126; 436/161; 436/173; 436/85; 250/281; 250/282; 250/288
[58] Field of Search ..................................... 436/124–126, 436/161, 173, 183, 85; 250/281, 282, 288

[56] References Cited

U.S. PATENT DOCUMENTS 5,493,115   2/1996   Deinzer et al. ........................ 250/281

OTHER PUBLICATIONS

I. K. Mun et al. *Anal. Chem.* 1977, 49, 1723–1726.
R. J. Anderegg *Anal. Chem.* 1981, 53, 2169–2171.
N. Gjøs et al, *Anal. Chem.* 1982, 54, 1316–1318.
J. L. LaBrosse et al. *J. Chromatog.* 1984, 314, 93–102.
D. R. Scott *Anal. Chem.* 1986, 58, 881–890.
H.–R. Buser *Anal. Chem.* 1986, 58, 2913–2919.
M. A. Dearth et al. *Environ. Sci. Technol.* 1991, 25, 245–254.
A. Jablonska et al. *J. Chromatog.* 1993, 647, 341–350.
H. C. Hollifield et al. *J. Assoc. Off. Anal. Chem*, 1978, 61, 537–544.
M. Oehme *Int. J. Mass Spectrom., Ion Phys.* 1983, 48, 287–290.
J.B. Pausch et al. *Rubber Chem. Technol.* 1983, 56, 1031–1044.
S.–Z Sha et al. *J. Chromatog.* 1984, 284, 157–165.
J. Milhaud *Chem. Phys, Lett.* 1985, 118, 167–173.
R. Kroneld *Bull. Environ. Contam. Toxicol.* 1985, 34, 486–496.
T. M. Trainor et al. *Anal. Chem.* 1987, 59, 601–610.
J.R. Donnelly et al. *Biomed. Environ. Mass Spectrom.* 1989, 18, 884–896.
B. Arbogast et al. *Org. Mass Spectrom.* 1990, 25, 191–196.
V. G. Voinov et al. *J. Chromatog.* 1991, 586, 360–362.
E. Kaisersberger et al. *ACS Symp. Ser.* 1994, 581, 74–80.
M. Oehme *Fresenius J. Anal. Chem.* 1994, 350, 544–554.
J. M. Curtis et al. *Int. J. Mass Spectrom., Ion Processes* 1997, 165–166, 625–639.
D. R. Zook, W. B. Knighton and E. P. Grimsrud, Dept. of Chemistry, Montana State University, Bozeman, MT, "Effect of Buffer Gas and Pressure Variations on the Formation of $Br_2^-$ in Reactions of Thermal Electrons with Dibrominated Hydrocarbons and Flurocarbons", *International Journal of Mass Spectrometry and Ion Processes*, 104 (1991) 63–80, Elsevier Science Publishers B.V., Amsterdam.

(List continued on next page.)

*Primary Examiner*—Arlen Soderquist
*Attorney, Agent, or Firm*—Estelle C. Bakun

[57] ABSTRACT

The present invention is directed to a method for determining the halogen toxicity level in a sample containing halogenated compounds, specifically halogen containing rubbers by utilizing thermal electrons formed inside a mass spectrometer operated at negative ion electron capture conditions. The method allows for detection of the toxic species from the parts per million level, down to the parts per billion levels. The method comprises the steps of (a) ionizing a reagent gas capable of producing thermal electrons having a thermal energy of 0 to 10 eV with the a polychromatic ion source of a mass spectrometer to produce thermal electrons having thermal energy of 0 to 10 eV, (b) capturing said thermal electrons with a halogen containing compound to form halogen atomic anions or halogen atomic cluster anions wherein said halogen containing compound has been passed through a gas chromatograph prior to said capturing of thermal electrons and wherein a mass spectrogram is obtained following said capturing of electrons, (c) speciating and quantifying said halogen atomic anions or halogen atomic cluster anions using a mass chromatogram produced from a combination of said gas chromatography and said mass spectrometer.

9 Claims, 5 Drawing Sheets

OTHER PUBLICATIONS

A. Ito, K. Matsumoto and T. Takeuchi, Dept. of Synthetic Chemistry, Faculty of Engineering, Nagoya University, Nagoya, Japan, "Negative Ion Mass Spectra of Chlorine–Containing Molecules", *Organic Mass Spectrometry*, 1972, vol.6, pp 1045–1049, Heyden & Son Limited. Printed in Northern Ireland.

S. Daishima, Y. Iida and F. Kanda, Dept. of Industrial Chemistry, Faculty of Engineering, Seikei University, Kichijoji Kitamachi, Musashino, Tokyo, Japan, The Ion Formation and the Detection Limits in Negative Ion Chemical Ionization Mass Spectrometry of Some Halogenated Compounds, *J. Trace and Microprobe Techniques*, 7 (1&2), 87–102 (1989).

A. Danon and A. Amirav, School of Chemistry, Sackler Faculty of Exact Sciences, Tel Aviv University, Tel–Aviv, Israel, "Hyperthermal Surface Ionization: A Novel Ion Source with Analytical Applications", *International Journal of Mass Spectrometry and Ion Processes*, (1990), 96(2), pp. 139–167, Elsevier Science Publishers B.V., Amsterdam. Printed in The Netherlands.

AN: 57(1):D159 ANABSTR (Abstract).
AN: 1996:126010 HCAPLUS (Abstract).
AN: 82:58246 TOXLIT (Abstract).
AN: 85104602 MEDLINE (Abstract).
AN: 1988:621632 HCAPLUS (Abstract).
AN: 76:19012 TOXLINE (Abstract).
AN: 1990:111152 HCAPLUS (Abstract).
AN: 1987:445908 HCAPLUS (Abstract).
AN: 46(8):C9 ANABSTR (Abstract).
AN: 1971:481588 HCAPLUS (Abstract).
AN: 77165567 MEDLINE (Abstract).
AN: 85:63497 TOXLINE (Abstract).
AN: 87:69233 TOXLIT (Abstract).
AN: 1984:138436 HCAPLUS (Abstract).
AN: 78:50474 TOXLIT (Abstract).
AN: 85253051 MEDLINE (Abstract).

DETECTION AND MONITORING OF TOXIC HALOGENATED COMPOUNDS

FIELD OF THE INVENTION

The instant invention is directed to a method for determining the level of halogenated toxins present in halogenated compounds, more specifically, halogenated rubbers, more particularly, bromobutyl rubbers.

BACKGROUND OF THE INVENTION

Each year millions of tons of bromobutyl and chlorobutyl rubber are produced and used by the tire industry. The processes utilized to prepare such rubbers involve the use of halogenated solvents, often recycled between the production cycles of bromobutyl and chlorobutyl rubbers, which contain species such as Br, $Br_2$, BrCl, and $Br_2Cl$ in order of increasing toxicity as substituents on compounds. These species must be removed from the resulting rubber to levels that will not pose a health threat or hazard to handlers of the rubbers.

Several techniques exist to determine the level of halogens in rubber, however, each has deficiencies. For example, Electron Capture Detectors and Hall Electrolytic Conductivity Detectors may be used, but they afford no differentiation between Br and Cl species. Atomic Emission Detectors are capable of differentiating Br from Cl, but they are incapable of differentiating or determining the number of halogen atoms in a molecule such as Br from $Br_2$. Because of the varying levels of toxicity of the various classes of halogen compounds, to obtain an accurate toxicity level, it is necessary to be able to differentiate between all halogenated species and quantify the levels of toxicity resulting from each.

U.S. Pat. No. 5,493,115 discloses a method for analyzing a sample for a compound of interest using mass analysis of ions produced by slow monochromatic electron beams. The sample itself is passed into an electron monochromater and ions of at least a subpopulation of the molecules are formed. The ions are then passed through a mass analyzer to obtain a spectrum to determine if the ions in the spectrum contain ions from the analyte. The patent mentions that a gas chromatograph may be used to separate the sample prior to passing it into the electron monochromater. No buffer gases are necessary.

There still is a need in the art for a method capable of accurately detecting the levels and types of the different toxic halogens in rubbers, specifically, bromobutyl rubbers, to ensure that rubber handlers are not exposed to unsafe levels of such toxins during production, handling, or further processing of the rubbers.

Though the instant invention is preferably utilized for bromobutyl rubbers, it can easily be extended to other halogen containing rubbers, resins, and chemicals by those skilled in the art, for example to chlorobutyl rubbers.

SUMMARY OF THE INVENTION

The instant invention uses a combination of gas chromatography and mass spectroscopy (referred to herein as GC/MS) to obtain mass chromatograms which can be utilized to speciate and quantify various halogenated species including halogen atomic anions and halogen cluster anions. The mass spectroscopy utilizes polychromatic thermal electrons which affords an increased sensitivity for detection of the halogenated species of concern allowing detection down to parts per billion levels.

Therefore, the present invention is directed to a method for determining the halogen toxicity level in a sample containing halogenated compounds, specifically halogen containing rubbers by utilizing thermal electrons formed inside a mass spectrometer operated at electron capture conditions to produce negative ions. The method allows for detection of the toxic species down to parts per billion levels.

The method comprises the steps of:

(a) ionizing a reagent gas capable of producing thermal electrons having a thermal energy of 0 to 10 eV with a polychromatic ion source of a mass spectrometer to produce thermal electrons having thermal energy of 0 to 10 eV;

(b) capturing said thermal electrons with a halogen containing compound to form halogen atomic anions or halogen atomic cluster anions wherein said halogen containing compound has been passed through a gas chromatograph prior to said capturing of thermal electrons and wherein a mass spectrogram is obtained following said capturing of electrons;

(c) speciating and quantifying said halogen atomic anions or halogen atomic cluster anions using a mass chromatogram produced from a combination of said gas chromatograph and said mass spectrometer.

As used herein a halogen atomic cluster anion is an ion containing a multiple unit, either the same or different, of halogen atoms, for example $Br_2$ and BrCl. A halogen atomic anion is a single halogen unit, such as $Cl^-$ and $Br^-$. Such clusters and anions are herein referred to as halogen species.

DETAILED DESCRIPTION OF THE INVENTION

Figure 1:
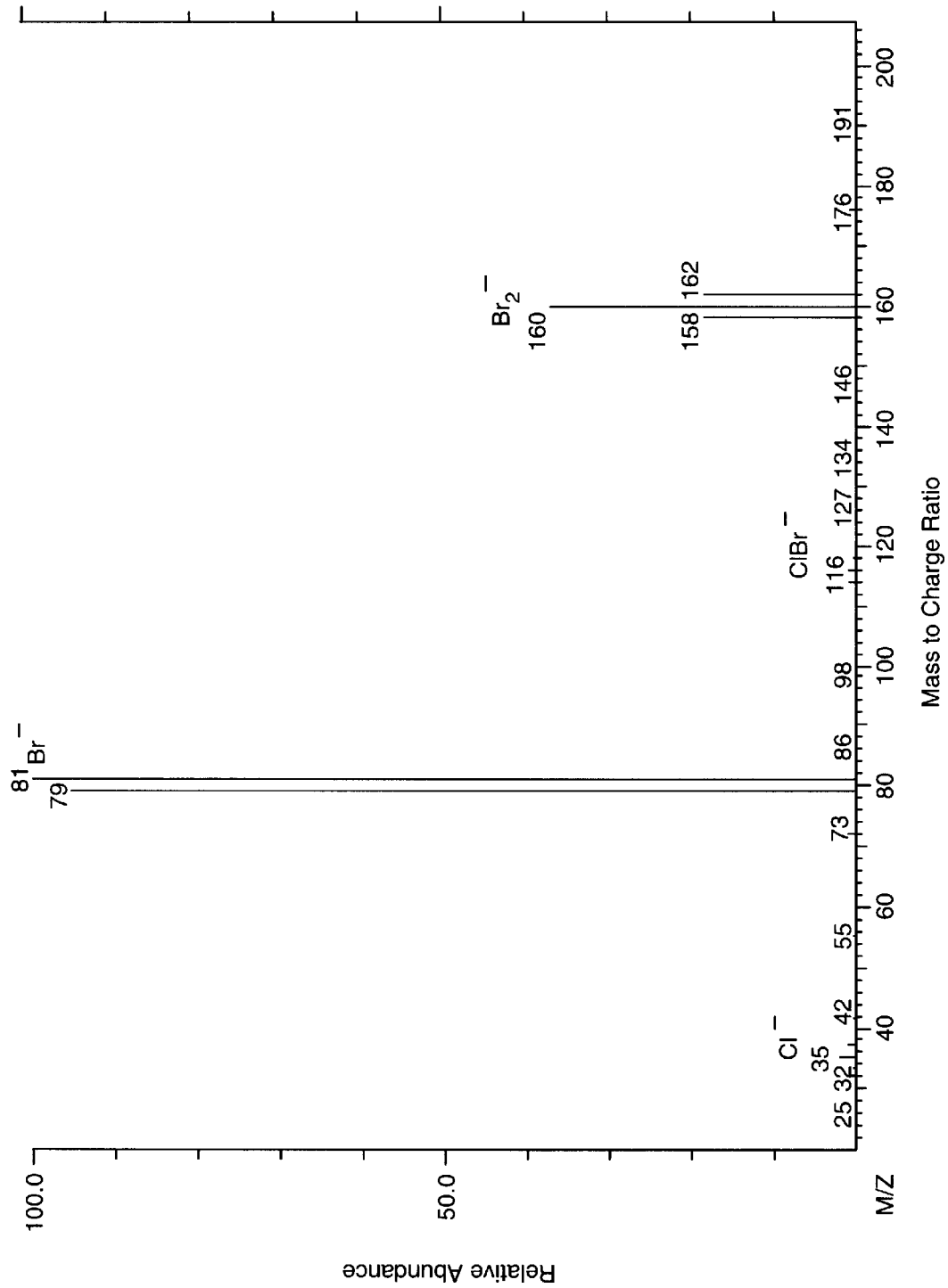
FIG. 1 is a negative ion electron capture mass spectrum of, 2-dibromo-3-chloro-2-methylpropane, showing the presence of $^{35}Cl$, $^{37}Cl$, $^{79}Br$, $^{81}Br$, $^{79}Br_2$(m/z 158), $^{79}Br^{81}Br$(m/z 160), $Br_2$(m/z 162), $^{35}Cl^{79}Br$(m/z 114), $^{35}Cl^{81}Br/^{37}Cl^{79}Br$ (m/z 116), and $^{37}Cl^{81}Br$(m/z/ 118) ions.

In the instant invention, a reagent gas is chosen which is capable of producing thermal electrons upon ionization in a mass spectrometer. The thermal electrons will have energies of 0 to 10 electron volts, preferably 0 to 5 eV. Such gases may include, but are not limited to methane, isobutane, and ammonia. However, one skilled in the art will recognize that any gas capable of producing the necessary thermal electrons may be used. The process is more easily understood by reference to the following equations which applicant though not wishing to be bound, believes to be the mechanism at play in the instant invention. For example, if methane were the chosen reagent gas the following is believed to occur:

Step 1: Generation of thermal electrons:

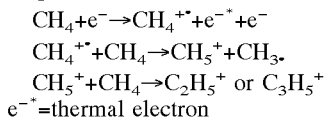

$e^{-*}$ = thermal electron

In this step, the reagent gas undergoes electron bombardment in the ion source of the mass spectrometer. This typically requires bombardment with an electron beam of about 50 to about 100 eV. However, any electron beam ionization source capable of producing thermal electrons from the reagent gas having energies of 0 to 10 eV can be utilized.

Step 2: Dissociative Capture of Thermal Electrons:

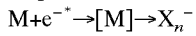

M = halogenated toxin containing compound $X_n^-$ = halogen atomic cluster anion, where n is a whole number $\geq 1$ In the second step, thermal electrons are captured by the halogen containing molecules, forming molecular anions followed by dissociative electron capture to form a halogen atomic anion or cluster anion.

The instant is preferentially utilized for non-aromatic halides. For non-aromatic halides, halogen atomic anions are formed via the electron capture dissociation mechanism due to the instability of the molecular anions. From a quantum mechanics point of view, an excess of electrons captured by aromatic halides occupies a more stable antibonding $\tau^*$ orbitals and can be stabilized. An excess electron captured by non-aromatic halides occupies a less stable anti-bonding $\sigma^*$ orbital at a much higher energy. With less orbital stability, and much more energy available than aromatic halides, instant dissociation occurs in non-aromatic halides leading to the formation of halogen anions. One skilled in the art will recognize this as negative ion chemical ionization (NICI).

For non-aromatic or conjugated compounds with halogen atoms at 1,2 ($\beta$-) or 1,4-($\delta$-) positions diatomic halogen anions are formed in addition to mono-atomic halogen anions; thus providing evidence of the presence of compounds containing a multiple unit of halogen. By multiple unit is meant more than one halogen of the same or different type, i.e. $Br_2$, $Cl_2$, $BrCl$ etc.

The conditions for operation of the gas chromatograph utilized herein are readily determinable by one skilled in the art. Any conditions capable of separating halogenated compounds from the sample being analyzed are acceptable. However, preferably, individual halogenated compounds will be separated from the sample and from each other. Additionally, the sample preparation utilized herein is readily accomplished by one skilled in the art. Indeed, any sample preparation which renders the halogen component of the sample being analyzed injectable into the gas chromatograph is acceptable. For instance, the halogenated compounds contained in rubber can be extracted by dissolving the rubber in a suitable solvent, preferably pentane or hexane, followed by precipitation of the bulk of the rubber by addition of a polar solvent such as acetone. The hexane/pentane solution would then be collected and analyzed as noted herein.

The GC/MS mass chromatograms obtained differentiate between cluster anions of both like and unlike halogen, such as $Br_2$ and $BrCl$. Prior art methods are incapable of such speciation. Considering that unlike clusters present the greatest toxicity, such speciation is important when detecting toxicity levels in halogen containing compounds. Additionally, from the chromatograms obtained, one skilled in the art can readily quantify, by known techniques, the amount of each type of atomic anion or atomic cluster anion present in a compound down to parts per billion levels. Such methods include peak integration followed by comparison with a standard reference for the species being integrated.

The method herein described can be used on line during the production of halogen containing products, such as rubbers. The method would be utilized on line in a process producing a product containing halogenated compounds and the speciation and quantification fed back to the steps of the process where halogens are introduced or formed and the process operating parameters modified in response to the feedback to obtain a desired halogen level in the finished product.

The invention will now be demonstrated with reference to the following examples which are merely illustrative and not meant to be limiting in any way.

EXAMPLE 1

Figure 2:
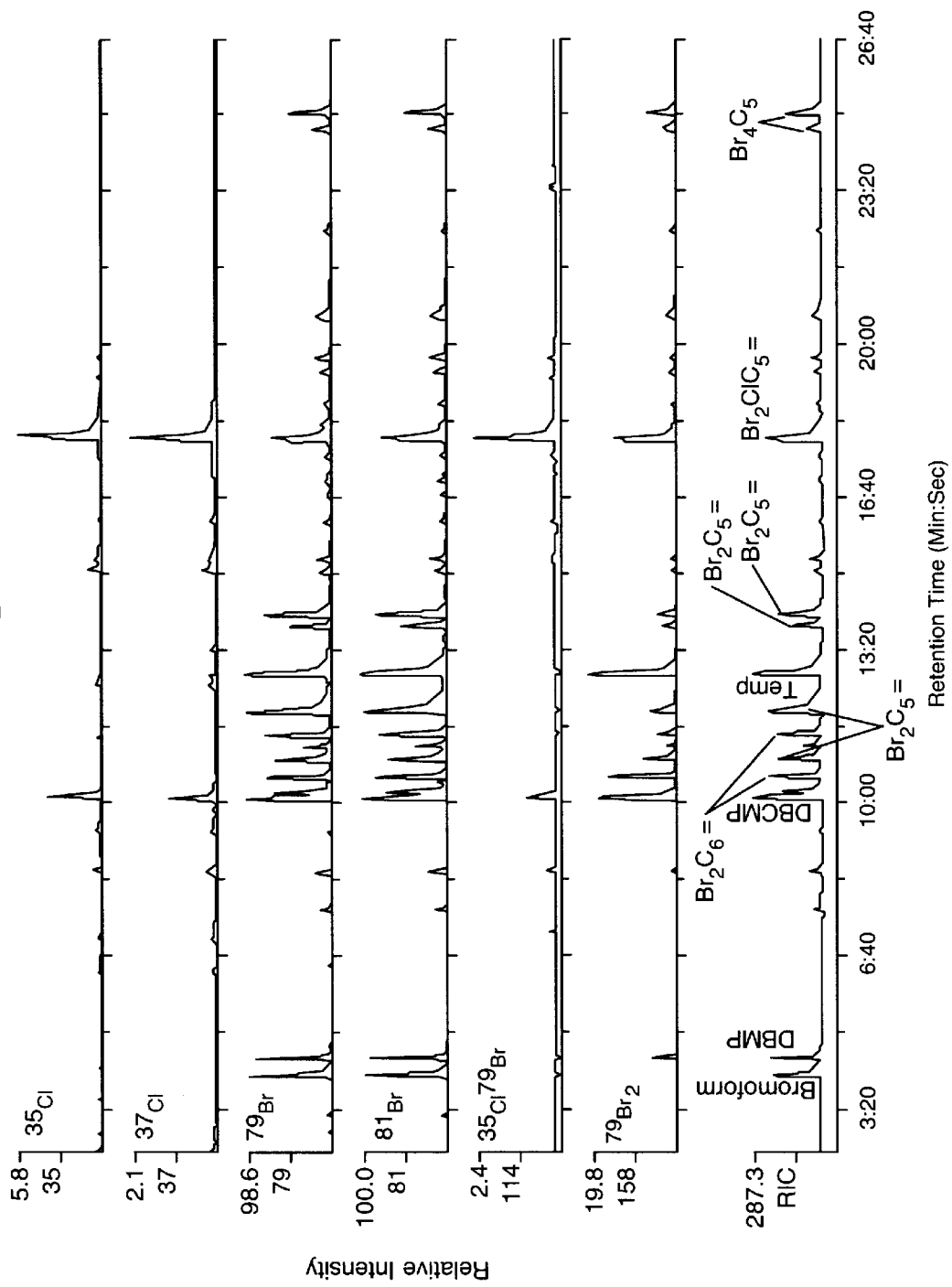
FIG. 2 shows mass chromatograms of $^{35}Cl$, $^{37}Cl$, $^{79}Br$, $^{81}Br$, $^{35}Cl^{79}Br$(m/z 114), and $^{79}Br_2$(m/z 158), and total ion chromatogram shown as the bottom trace with compound identification. All chlorinated compounds yield $^{35}Cl$ and $^{37}Cl$ ions, brominated compounds yield $^{79}Br$ and $^{81}Br$, compounds containing both chlorine and bromine yield $^{35}Cl^{79}Br$ and compounds containing more than one bromine yield $^{79}Br_2$ ions.

A blend containing 100 ppm each of bromoform, 1,2-dibromo-2-methylpropane ($Br_2C_4$), 1,2-dibromo-3-chloro-2-methylpropane (DBCMP,$Br_2ClC_4$), 1,2,3-tribromo-2-methylpropane ($Br_3C_4$), 1,2-dibromohexane ($Br_2C_6$), 2,3-dibromohexane ($Br_2C_6$), 3,4-dibromohexane ($Br_2C_6$), and isoprene dibromide ($Br_2C_5^-$) was tested using negative ion chemical ionization. For mono-halogenated compounds, halogen anions predominate in the instant invention. For halogen containing compounds containing multiple units of halogen (two or more, of the same or different halogen atoms halogen atom cluster anions are also present. A typical spectrum for compounds containing halogen atoms at 1,2 or 1,4 positions is given in FIG. 1 which is a NICI spectrum of DBCMP. Only anions containing halogen atoms and atom clusters are obtained for halogenated compounds as a result of electron capture followed by dissociation. For example, chlorinated compounds yield $^{35}Cl$ and $^{37}Cl$ ions in an isotopic ratio of natural abundance of 3 to 1, while brominated compounds yield $^{79}Br$ and $^{81}Br$ in an isotopic ratio of natural abundance of 1 to 1. Most importantly, for compounds containing more than two bromine atoms, an atomic cluster of $^{79}Br_2$(m/z 158), $^{79}Br^{81}Br$(m/z 160) and $Br_2$(m/z 162) is also present. Similarly an atomic cluster of $^{35}Cl^{79}Br$ (m/z 114), $^{35}Cl^{81}Br/^{37}Cl^{79}Br$ (m/z 116) and $^{37}Cl^{81}Br$(m/z 118) is formed for compounds containing both chlorine and bromine. Using gas chromatography to separate individual components in a mixture, the presence of these halogenated ionic species can be detected by mass chromatograms of elements and their atomic clusters, shown in FIG. 2. For instance, the m/z 114 and 158 (or 160) mass chromatograms in NICI can be used as sensitive and selective means to monitor low levels of toxic compounds containing at least one bromine and one chlorine and at least two bromine atoms, respectively. Note that bromoform does not yield $Br_2$ anions because all of the bromine atoms are attached to the same carbon. The data shown are the results from a full scan mode from mass 35 to 500. Using this mode, low ppm levels of halogenated compounds can be detected. The sensitivity (or detection limit) can be increased further (about two orders of magnitude) by monitoring only a few selected ion species. Hence, a detection of sub-ppm levels of multiple halogenated species can be achieved using a selected ion monitoring that is below what occupational exposure levels require.

Figure 3:
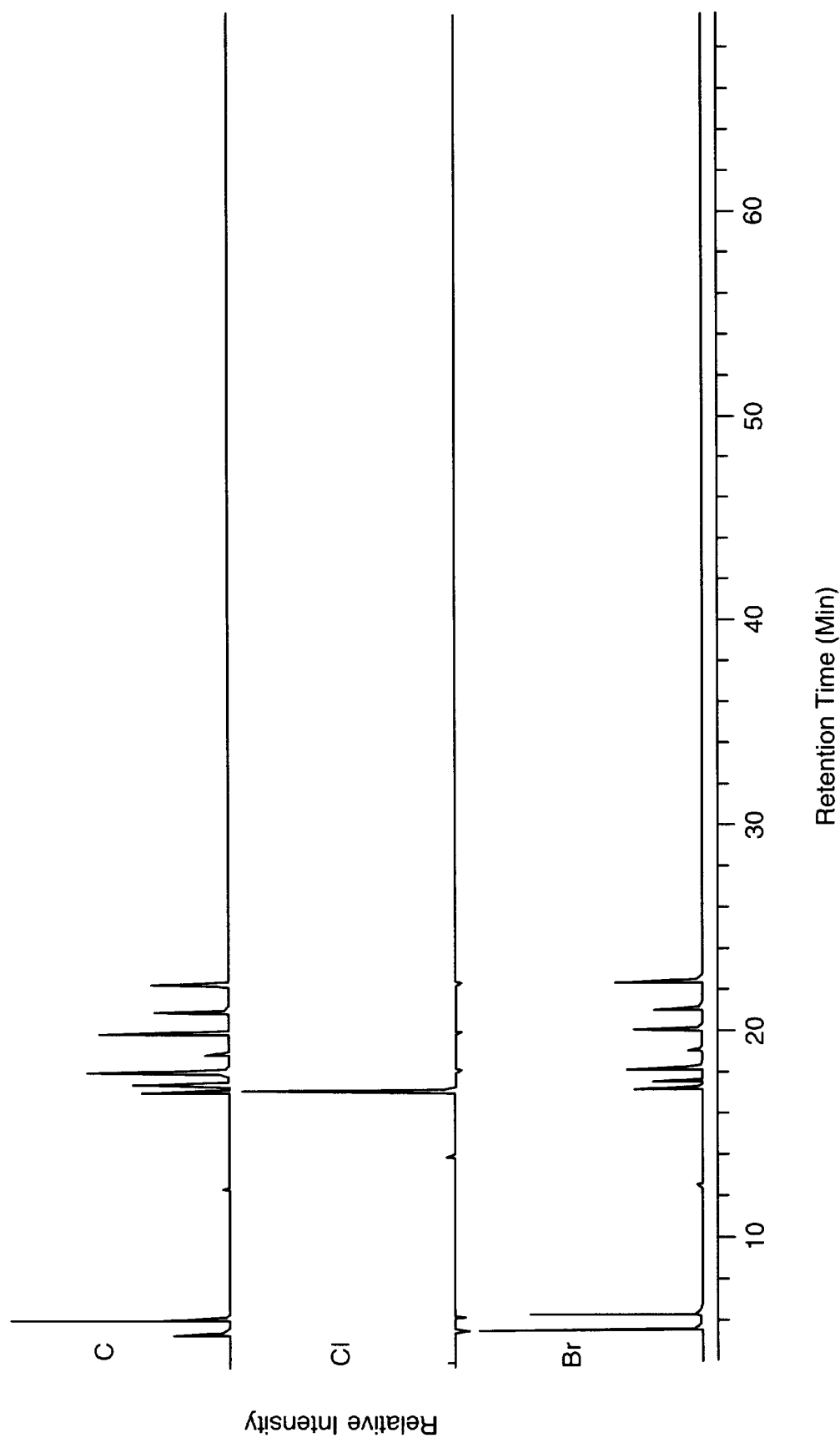
FIG. 3 is a gas chromatograph-atomic emission detection of a blend showing carbon, chlorine, and bromine channels for compound detection.
Figure 4:
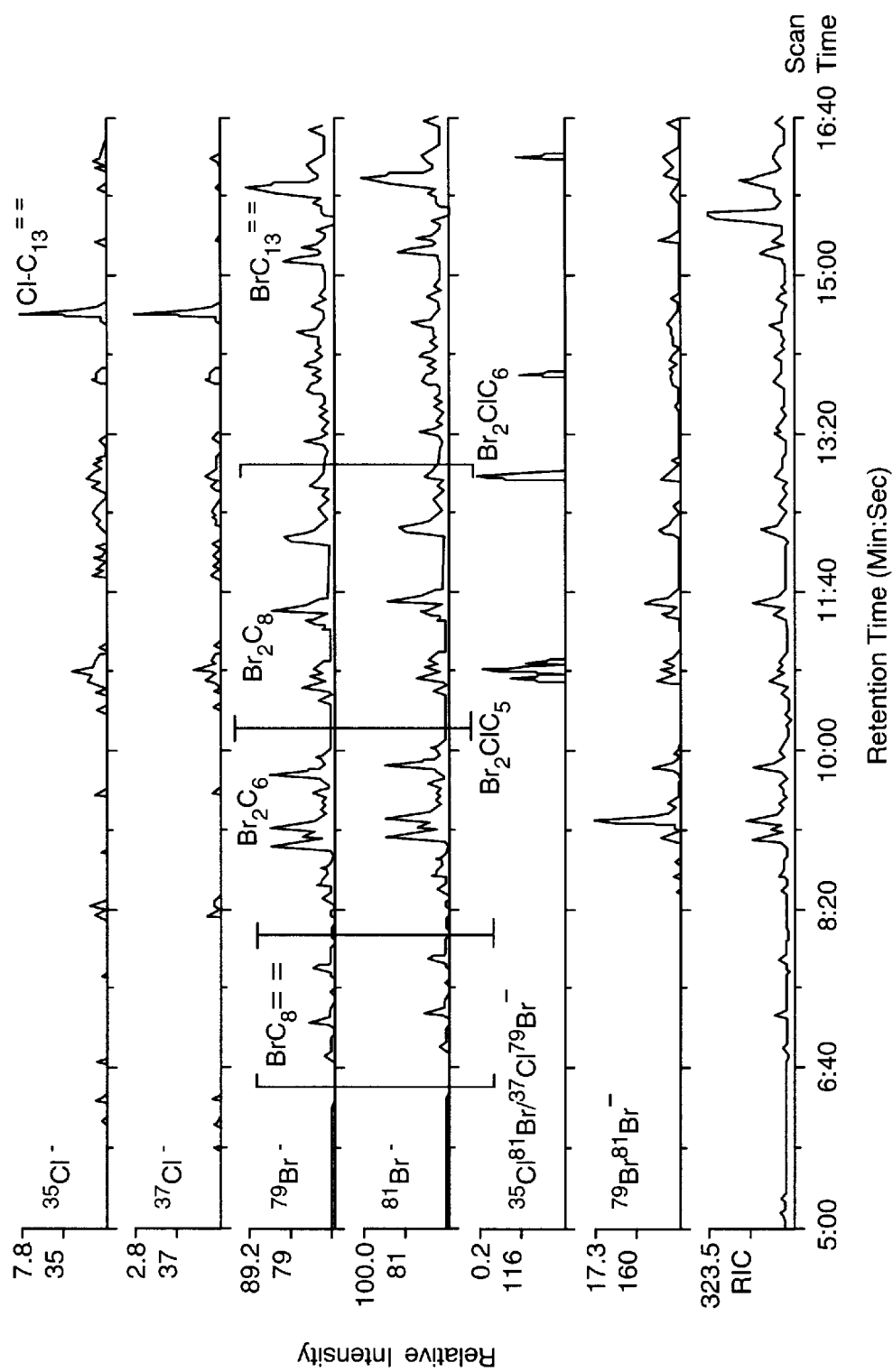
FIG. 4 is a mass chromatogram of $^{35}Cl$, $^{37}Cl$, $^{79}Br$, $^{81}Br$, $^{35}Cl^{79}Br$(m/z 116), and $^{79}Br^{81}Br$(m/z 160) and total ion chromatogram (shown in the bottom trace) of a bromobutyl rubber extract. The most abundant halogenated compounds are present in a few parts per million.
Figure 5:
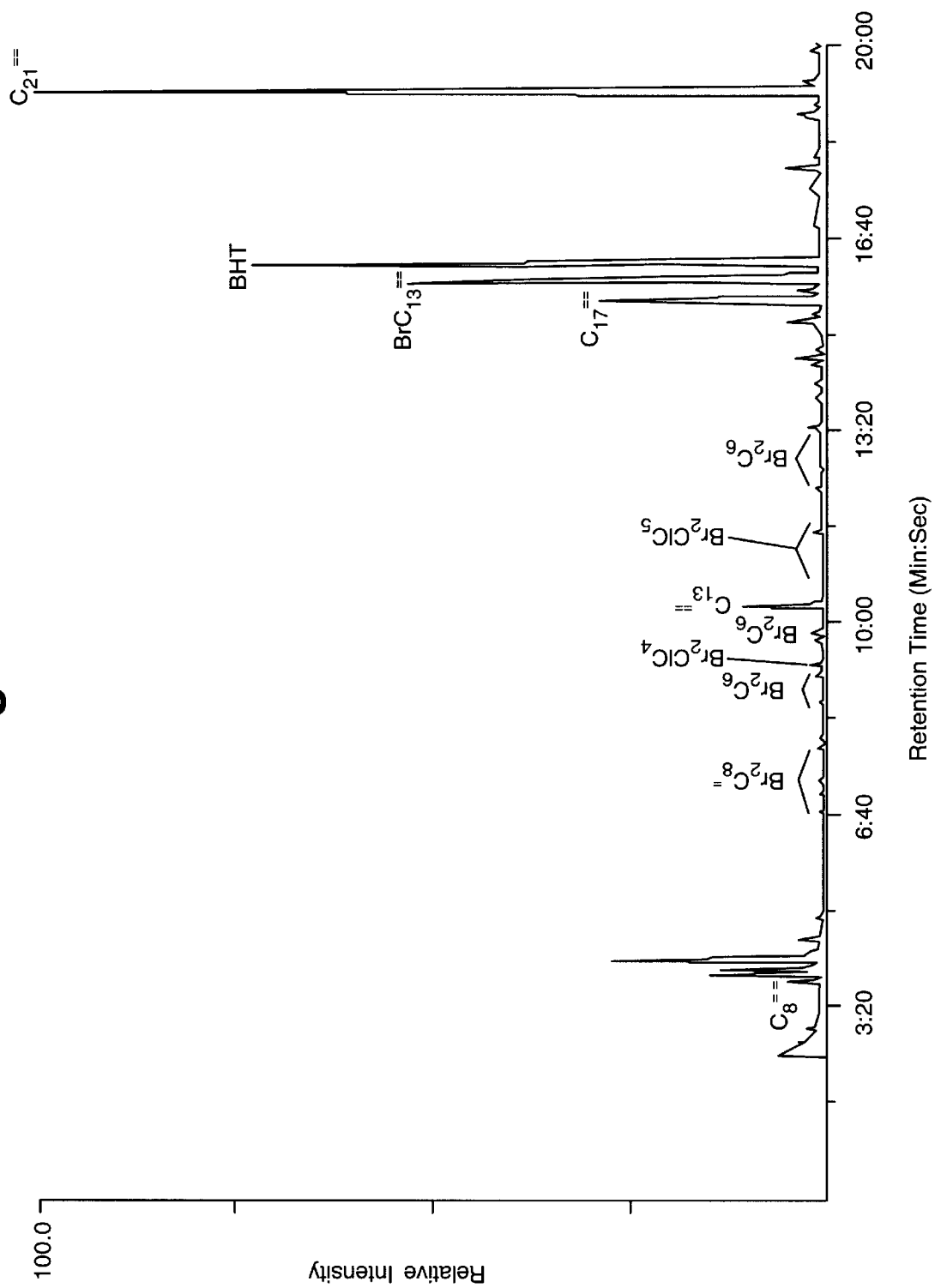
FIG. 5 is a GC/MS total ion chromatogramn obtained from electron ionization showing that halogenated compounds are present in trace amounts.

FIG. 3 shows gas chromatographic results using atomic emission detection (AED). As an example for compounds containing both chlorine and bromine, 1,2-dibromo-3-chloro-2-methylpropane (DBCMP, $Br_2ClC_4$) gives signals in both chlorine and bromine channels. It is however, not clear whether these two elements are present in the same molecule or in two different molecules having the same retention time. In addition, dibromo compounds cannot be differentiated from monobromo compounds by AED. This demonstrates the advantage of using the instant invention.

EXAMPLE 2

Two grams of bromobutyl rubber was dissolved in 50 ml of hexane for 3–4 hours until all the rubber was dissolved. 30 ml of acetone was added to the hexane solution to drop the rubber off. The remaining hexane/acetone solution was analyzed by a gas chromatograph coupled with a mass spectrometer operated in a NICI mode. The presence of halogenated compounds in trace levels (on the order of a few ppm) is readily detected. If needed, the sensitivity can be further improved by using selected ion monitoring for only a few ions such as mass 114 for bromochloro and 160 for dibromo compounds respectively. Identification of these compounds were obtained from their electron ionization (El) spectra. A chromatogram obtained at El conditions shows that the halogenated species are in trace amounts. The halogenated compounds of concern are "buried" under many more abundant non-halogenated compounds and would be difficult to detect by other analytical means.

What is claimed is:

1. A method for detecting and quantifying halogen levels in a sample containing non-aromatic halogenated compounds wherein said method distinguishes between halogenated species selected from the group consisting of $Br_2$, $BrCl$, $Br_2Cl$, and mixtures thereof, comprising the steps of:
    (a) ionizing a reagent gas capable of producing thermal electrons having a thermal energy of 0 to 10 eV with a polychromatic ion source of a mass spectrometer to produce thermal electrons having thermal energy of 0 to 10 eV;
    (b) capturing said thermal electrons with a non-aromatic halogen containing compound to form at least one halogen atomic cluster anions, wherein said non-aromatic halogen containing compound has been passed through a gas chromatograph prior to said capturing of thermal electrons and wherein a mass spectrogram is obtained following said capturing of electrons;
    (c) speciating and quantifying said halogen atomic cluster anions using a mass chromatogram produced from a combination of said gas chromatograph and said mass spectrometer.

2. The method of claim 1 wherein the amount of said non-aromatic containing compound containing said halogenated species selected from the group consisting of $Br_2$, $BrCl$, $Br_2Cl$ is determined.

3. The method of claim 1 wherein said reagent gas is selected from methane, isobutane, and ammonia gas.

4. The method of claim 1 wherein said sample is a rubber.

5. The method according to claim 4 wherein said rubber is a bromobutyl rubber or chlorobutyl rubber.

6. The method according to claim 5 wherein said rubber is bromobutyl rubber.

7. The method of claim 1 wherein said mass to charge ratio (m/z) of said $Br_2$ and $BrCl$ species are $^{79}Br_2$(m/z 158), $^{79}Br^{81}Br$(m/z 160, and $^{81}Br_2$(m/z 162), and for $^{35}Cl^{79}Br$(m/z 114), $^{35}Cl^{81}Br/^{37}Cl^{79}Br$(m/z 116) and $^{37}Cl^{81}Br$(m/z 118).

8. The method of claim 1 wherein said quantification ranges from parts per million to parts per billion levels.

9. The method of claim 1 wherein said method is utilized on line in a process producing a product containing halogenated compounds and the speciation and quantification is fed back to the steps of the process where halogens are introduced or formed and the process operating parameters modified in response to said feedback to obtain a desired halogen level in the finished product.

* * * * *